United States Patent [19]

Holmgren

[11] Patent Number: 5,733,439
[45] Date of Patent: Mar. 31, 1998

[54] HYDROCARBON CONVERSION PROCESSES USING SUBSTITUTED FLUORIDE SMECTITE CLAYS

[75] Inventor: Jennifer S. Holmgren, Bloomingdale, Ill.

[73] Assignee: UOP, Des Plaines, Ill.

[21] Appl. No.: 571,665

[22] Filed: Dec. 13, 1995

Related U.S. Application Data

[63] Continuation-in-part of Ser. No. 214,507, Mar. 18, 1994, Pat. No. 5,503,819.

[51] Int. Cl.$^6$ .............. C10G 47/02; C07C 2/58; C07C 2/02
[52] U.S. Cl. .......... 208/111; 208/120; 208/135; 585/709; 585/721; 585/467; 585/468; 585/530; 585/531; 585/533; 585/653; 585/375
[58] Field of Search ................ 208/111, 120, 208/135; 585/709, 721, 467, 468, 530, 531, 533, 653, 375

[56] References Cited

U.S. PATENT DOCUMENTS

| | | | |
|---|---|---|---|
| 3,855,147 | 12/1974 | Granquist | 252/317 |
| 4,499,319 | 2/1985 | Ballantine et al. | 585/467 |
| 4,605,806 | 8/1986 | Ballantine et al. | 585/467 |
| 4,775,461 | 10/1988 | Harris et al. | 208/120 |
| 5,059,568 | 10/1991 | McCauley | 502/65 |
| 5,089,458 | 2/1992 | Breukelaar et al. | 502/63 |
| 5,139,648 | 8/1992 | Lambert | 208/111 |
| 5,248,644 | 9/1993 | Johnson et al. | 502/84 |
| 5,409,597 | 4/1995 | Holmgren | 208/111 |

FOREIGN PATENT DOCUMENTS

317006A2  5/1989  European Pat. Off.

*Primary Examiner*—Walter D. Griffin
*Attorney, Agent, or Firm*—Thomas K. McBride; Eugene I. Snyder; Frank S. Molinaro

[57] ABSTRACT

Hydrocarbon conversion processes, e.g., alkylation, are disclosed and claimed which use as the catalyst novel fluoride containing substituted smectite clays. The clay has the formula $$A_x(M_yM'_{4-y})(Si_{8-t}M_tM'_v)O_{20}(OH)_{4-u}F_u$$

where A is a cation, M and M' are metals having a +3 oxidation state, each selected from the group consisting of aluminum, gallium, iron and chromium, x is the moles of A, y is the moles of M, t and v are the moles of M and M' in the tetrahedral layer and t+v=x and u is the moles of F. The clay composition may be used as is or after pillaring to catalyze hydrocarbon conversion processes such as alkylation.

12 Claims, No Drawings

HYDROCARBON CONVERSION PROCESSES USING SUBSTITUTED FLUORIDE SMECTITE CLAYS

CROSS REFERENCE TO RELATED APPLICATION

This application is a Continuation-in-part of U.S. application Ser. No. 08/214,507 filed on Mar. 18, 1994, now U.S. Pat. No. 5,503,819, which is incorporated by reference.

FIELD OF THE INVENTION

This invention relates to hydrocarbon conversion processes using novel gallium, iron or chromium substituted fluoride smectite clay compositions.

BACKGROUND OF THE INVENTION

Naturally occurring clays such as dioctahedral smectites are composed of semicrystalline aluminosilicate layers (lamellae) held together by Van der Waals and electrostatic forces. Anionic charges on the siliceous layers are neutralized by cations in the interlamellar spaces. These cations are usually sodium, calcium, or potassium. When these cations are large oligomers of inorganic cations such as $Fe^{+3}$, $Cr^{+3}$ or when they are metal hydroxy polymer cations such as $(Al_{13}O_4(OH)_{24}(H_2O)_{12})^{7+}$ or $(Zr(OH)_2 \cdot 4H_2O)_4^{8+}$, they act as pillars, propping the clay layers apart to afford a pillared layered clay. Upon heating, these oligomers or polymers are convened to the metal oxide, thus preventing the collapse of the clay layers and thus pillaring the clay.

Smectite clays are a family of clays which include as its members montmorillonite, beidellite, nontronite, saponite, hectorite and sauconite. Of these materials beidellite, hectorite and saponite have been prepared synthetically. Saponite contains magnesium, aluminum and silicon and is represented by the formula $$A_x(Mg_6)(Si_{8-x}Al_x)(O_{20})(OH)_4$$

where A is a cation such as an alkali metal cation. There are reports that saponite can be prepared by substituting fluoride ions for the hydroxyl ions. Thus, U.S. Pat. No. 3,855,147 discloses a process for preparing a saponite material where a fraction of the hydroxyl groups are replaced by fluorides. Similarly U.S. Pat. No. 5,089,458 discloses a saponite derivative in which some of the magnesium has been replaced by a divalent metal ion and some of the hydroxyl groups have been replaced by fluorides. Finally, European Patent Publication 317,006A2 discloses the preparation of a saponite in which fluorides are used instead of hydroxyl.

In contrast to what is disclosed in the prior art, applicant has prepared a fluorided smectite clay in which the metal in the octahedral layer is a metal having a +3 oxidation state and selected from gallium, iron, chromium mixtures thereof or mixtures of aluminum and one or more of the above-named metals. The tetrahedral layer contains silicon plus one or more of the +3 metals enumerated above. These compositions are prepared by preparing a mixture which contains reactive sources of the desired metals, a cation salt and a fluoride source and reacting the mixture at a pH of about 4 to about 9 and at a temperature of about 150° C. to about 300° C.

SUMMARY OF THE INVENTION

This invention relates to a hydrocarbon conversion process using a novel smectite clay. Accordingly, one embodiment of the invention is a hydrocarbon conversion process comprising contacting a hydrocarbon feed under hydrocarbon conversion conditions with a catalyst to give a hydroconverted product, the catalyst comprising a smectite layered clay composition having the empirical formula $$A_x(M_yM'_{4-y})(Si_{8-u}M_tM'_v)O_{20}(OH)_{4-u}F_u$$

where A is a cation, x is the moles of the cation and varies from about 0.1 to about 2.0, M and M' are metals having a +3 oxidation state, each metal selected from the group consisting of aluminum, gallium, iron and chromium, y is the moles of M and varies from 0 to about 4, except that when M or M' is aluminum, y has a value from greater than 0 to about 4, t is the moles of M and varies from about 0 to about 2, v is the moles of M' and varies from about 0 to about 2 and t+v=x, and u is the moles of F and varies from about 0.1 to about 3.5.

Other objects and embodiments will become more apparent after a more detailed description of the invention.

DETAILED DESCRIPTION OF THE INVENTION

The clay composition used in the process of the present invention is represented by the empirical formula $$A_x(M_yM'_{4-y})(Si_{8-u}M_tM'_v)O_{20}(OH)_{4-u}F_u$$

In this empirical formula A is a cation selected from the group consisting of alkali metals, quaternary ammonium ions, quaternary phosphonium ions and mixtures thereof, and x is the moles of A and varies from about 0.1 to about 2.0. The M and M' metals are metals having a +3 oxidation state and are each selected from the group consisting of aluminum, gallium, iron and chromium. The moles of M is represented by y which has a value of zero to about 4. However, when M or M' is aluminum, then y must be greater than zero. That is, when aluminum is present, a second +3 metal must also be present in the formula. The moles of M and M' found in the tetrahedral layers are designated by "t" and "v", each of which has a value from about 0 to about 2 and t+v=x. Finally, the moles of fluorine present is represented by u which varies from about 0.1 to about 3.5. Other characteristics of the smectite clay of this invention will be described hereinafter.

The clay composition of the instant invention is prepared from a reaction mixture which contains reactive sources of the desired metals, a salt of the cation, a fluoride source and water. The reaction mixture is expressed in terms of molar ratios by the formula $$a\ R:wSiO_2:cM_2O_3:sM'_2O_3:rF^-:bH_2O$$

where R is at least one cation salt, a is the moles of R and is chosen such that the ratio of a:w varies from about 0.1 to about 5, w is the moles of $SiO_2$ and varies from about 0.1 to about 10, z is the moles of $M_2O_3$ and varies from about 0 to about 5, s is the moles of $M'_2O_3$ and varies from about 0 to about 5, r is the moles of fluoride and is chosen such that the ratio of Si:F is greater than 1 to about 20 and b is the moles of water and varies from about 10 to about 500.

The cation salts which can be used in preparing the clay composition of this invention are alkali metal compounds, quaternary ammonium or quaternary phos-phonium compounds, the latter two compounds having the formula $R'_4M^+X^-$ where R' is an alkyl group containing from 1 to 8 carbon atoms or an aryl group, M is nitrogen or phosphorus and X is carbonate, hydroxyl or halide. Illustrative of the alkali metal compounds are the chloride, fluoride, hydroxide and carbonate salts of sodium, potassium and lithium. Illustrative of the quaternary compounds which can be used are the hydroxide, carbonate, chloride, bromide, fluoride and iodide salts of the following cations: tetramethylammonium; tetraethylammonium; tetrapropylammonium; tetrabutylammonium; tetra-t-butylammonium; tetrapentylammonium; tetra-phenylammonium; tetramethylphosphonium; tetraethylphosphonium; tetrapropylphosphonium and tetraphenylphosphonium. It should be pointed out that mixtures of cation salts can also be used to prepare compositions of this invention. The amount of cation salt that is necessary is determined by the amount of silicon present in the mixture. It is necessary that the ratio of the moles of cation salt to the moles of silicon in the mixture vary from about 1 to about 20 and preferably from about 5 to about 10.

Another necessary component of the reaction mixture is a reactive source of the desired +3 metals. By reactive is meant a compound that is not fully condensed. That is, the compound still contains one or more hydroxide groups or is hydrated. Illustrative examples of reactive sources of aluminum include sodium aluminate, boehmite alumina, gibbsite alumina, aluminum hydroxide, aluminum alkoxides and mixtures thereof. If aluminum hydroxide is used it is preferred to use freshly prepared aluminum hydroxide. Specific examples of aluminum alkoxides include aluminum isopropoxide and aluminum t-butoxide. Examples of reactive sources of iron, gallium and chromium are gallium hydroxide ($Ga(OH)_3$), chromium hydroxide ($Cr(OH)_3$), chromium chloride ($CrCl_3$), gallium sulfate ($Ga_2(SO_4)_3$), iron hydroxide ($Fe(OH)_3$), iron chloride ($FeCl_3$) and sodium gallium oxide ($NaGaO_2$).

A further necessary component of the reactive mixture is a reactive source of silicon. Illustrative of the reactive sources of silicon are colloidal silica, fumed silica, silicic acid, silicon alkoxide and mixtures thereof. Specific examples of silicon alkoxides include tetraethylorthosilicate and tetramethylorthosilicate. Finally, it is necessary that the reaction mixture contain a fluoride source, illustrative examples of which are: hydrogen fluoride, sodium fluoride, potassium fluoride, ammonium fluoride and ammonium bifluoride. The amount of fluoride is chosen, such that the Si:F ratio is greater than 0.4 to about 6 and preferably greater than 0.8 to about 3.

Having formed the reaction mixture, it is reacted at reaction conditions for an effective time to provide the desired composition. The reaction conditions necessary to produce the desired smectite layered clay include a pH of about 4 to about 9 and preferably a pH of about 4 to about 7. The presence of the fluoride allows the $SiO_2$ to be mineralized. In addition to the necessary pH, it is also necessary to carry out the reaction at a temperature of at least 150° C. or greater, preferably in the range of about 150° C. to about 300° C. and especially in the range of about 150° to about 200° C. Finally the reaction mixture is reacted under the above described reaction conditions at an effective time which ranges from about 1 to about 20 days in order to produce the desired smectite clay.

The smectite clay composition of this invention can be used as is or it can be pillared to catalyze various hydrocarbon processes. It is preferred to catalyze the various hydrocarbon process with a pillared beidellite clay. The clay can be pillared using methods well known in the art. Examples of pillars which are well known in the art are alumina, rare earth containing alumina, $ZrO_2$, $TiO_2$, $Cr_2O_3$, $SiO_2$, Si/Al (silica/alumina) and mixtures thereof. It should be pointed out that silica/alumina is not a physical mixture of silica and alumina, but is instead a cogelled or coprecipitated material containing silica and alumina which is acidic and amorphous. Silica/alumina materials are described in U.S. Pat. Nos.: 3,274,124; 3,909,450 and 4,988,659, all of which are incorporated by reference. As stated, these pillars are introduced by combining the clay with an oligomer or polymer of the desired cation or mixture of cations at reaction conditions. For example, alumina pillars may be introduced by using aluminum chlorohydrate. Aluminum chlorohydrate (ACH), also known as aluminum chlorohydroxide, is a polymeric metal complex having the empirical formula

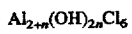

$$Al_{2+n}(OH)_{2n}Cl_6$$

where n has a value of about 4 to 12. The preparation of this aluminum polymer is generally known to those skilled in the art. See, for example: Tsuitida and Kobayashi, *J. Chem. Soc. Japan* (Pure Chem. Sect.), 64, 1268 (1943). Inoue, Osugi and Kanaji, *J. Chem. Soc. Japan* (Ind. Chem. Sec.), 61, 407 (1958).

A rare earth ACH is an ACH as described above which is modified to include one or more rare earth elements such as cerium, lanthanum, neodymium, europium, etc (all U.S. Pat. No. 4,952,544 which is incorporated by reference). The ACH polymer is modified with the rare earth by adding a soluble rare earth salt, preferably a water soluble rare earth salt. Examples of rare earth salts are the nitrates, halides, sulfates and acetates. Preferred rare earth elements are cerium and lanthanum with cerium nitrate and lanthanum nitrate being the preferred salts. The rare earth is introduced into the polymer or oligomer structure by mixing the rare earth salt either in solution (water preferred) or as a solid with the ACH. The mixture is refluxed at a temperature of about 105° to about 145° C. for a time of about 24 to about 100 hours. The molar ratio of rare earth (expressed as oxide, e.g., $CeO_2$) to alumina ($Al_2O_3$) in the solution prior to refluxing is from about 1:52 to about 1:1.

Descriptions of oligomers or polymers of the other pillaring materials can be found in the following references: 1) Si/Al—U.S. Pat. No. 4,176,090; 2) zirconia—*Clays and Clay Minerals*, 27, 119 (1979) and U.S. Pat. No. 4,176,090; 3) titania—U.S. Pat. No. 4,176,090; 4) chromium oxide—U.S. Pat. No. 4,216,188 and 5) silicon oxide—U.S. Pat. No. 4,367,163, all of which are incorporated by reference.

These pillared clays are prepared by means well known in the art such as adding the smectite clay to a solution containing a pillar precursor, i.e., oligomer or polymer, stirring, filtering, redispersing with water (one or more times), isolating, drying and calcining at about 300° to about 800° for a time sufficient to fix the structure (preferably about 3 hours).

If desired, the pillars can be fluorided by treating the pillared clay with a solution of a fluoride compound. Examples of fluoride compounds include ammonium fluorosilicate, ammonium bifluoride and ammonium fluoride. The fluoriding process involves taking the calcined pillared clay and dispersing it in water to form a slurry. To this slurry, there is added a solution (aqueous) of the desired fluoride compound. The fluoride containing slurry is now heated with stirring. The slurry can be heated to evaporate the water which effectively impregnates the fluoride onto the pillars (impregnation method). Alternatively, the slurry is heated up to a temperature of about 60° C. to about 90° C. for a time of about 30 minutes to about 6 hours without evaporation of the water (slurry method). If the water is not evaporated, the slurry is filtered and the clay is washed with from about 5 liters to about 20 liters of water. Regardless of whether the slurry or impregnation method is used, the isolated clay is dried and then calcined at a temperature of about 300° C. to about 600° C. for a time of about 1 hour to about 16 hours. This process results in some or all of the hydroxyls on the oligomers being substituted with fluorides.

As stated, smectite clay compositions are used to catalyze hydrocarbon conversion processes such as alkylation, cracking, hydrocracking, ester formation, dimerization, oligomerization, etc. It is particularly preferred to use the clay compositions of this invention whether pillared or non-pillared to catalyze alkylation, oligomerization and hydrocracking processes. The conditions necessary to carry out alkylation of aromatic compounds are well known and are disclosed, for example, in U.S. Pat. Nos. 3,965,043 and 3,979,331 which are incorporated by reference. Generally the process can be carried out in a batch type or a continuous type operation. In a batch type process, the catalyst, aromatic compound and alkylating agent are placed in an autoclave and the pressure increased, if necessary, in order to effect the reaction in the liquid phase. An excess amount of aromatic compound should be present, preferably in a range of about 2:1 to about 20:1 moles of aromatic compound per mole of alkylating agent. The reaction is carried out at an elevated temperature since the rate of alkylation is undesirably low at room temperature. Preferably the temperature is in the range of about 40° to about 200° C. The process is carried out for a time of about 0.5 to about 4 hours, after which the product is separated from the starting materials by conventional means.

If it is desired to carry out the process in a continuous manner, the catalyst is placed in a reactor which is heated to the desired operating temperature and the pressure increased above atmospheric, if necessary. The aromatic compound and alkylating agent are flowed over the catalyst bed at a predetermined liquid hourly space velocity sufficient to effect alkylation. The effluent is continuously withdrawn and conventional separation means used to isolate the desired product.

Hydrocracking conditions typically include a temperature in the range of 400° to 1200° F. (204°–649° C.), preferably between 600° and 950° F. (316°–510° C.). Reaction pressures are in the range of atmospheric to about 3,500 psig (24,132 kPa g), preferably between 200 and 3000 psig (1379–20,685 kPa g). Contact times usually correspond to liquid hourly space velocities (LHSV) in the range of about $0.1\ hr^{-1}$ to $15\ hr^{-1}$, preferably between about 0.2 and $3\ hr^{-1}$. Hydrogen circulation rates are in the range of 1,000 to 50,000 standard cubic feet (scf) per barrel of charge (178–8,888 std. $m^3/m^3$), preferably between 2,000 and 30,000 scf per barrel of charge (355–5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the clay composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Oligomerization of olefins is well known in the art. Generally, oligomerization of olefins containing from 2 to about 6 carbon atoms such as ethylene, propylene, butene-1, butene-2, pentene-1, pentene-2, pentene-3 may be effected by treating the olefin in the presence of a catalyst at oligomerization conditions which will include a temperature in the range of from about −20° C. to about 200° C., the preferred range being from about 30° C. to about 100° C., and a pressure in the range of from about 2413 kPa (ga) (350 psig) to about 6895 kPa (ga) (1,000 psig). The pressure which is utilized may be the autogenous pressure provided for by the feedstock, if in gaseous phase, or, the feedstock may supply only a partial pressure, the remainder of said pressure being provided by the introduction of an inert gas such as nitrogen, helium, argon, etc. into the reaction zone. The oligomerization reaction may be carried out either in a batch or continuous mode.

The following examples are presented in illustration of this invention and are not intended as undue limitations on the generally broad scope of the invention as set out in the appended claims.

EXAMPLE 1

A slurry was prepared by mixing 25 g of $Ga_2(SO_4)_3$ in 220 g of deionized water and stirring for 2 hours. To this slurry there was added a solution of 17 g of $NH_4OH$ in 150 g of water which resulted in a gelatinous white precipitate being immediately formed. The gel was homogenized for 10 minutes and then the solid was recovered by centrifugation and finally washed with deionized water.

EXAMPLE 2

In a three neck flask there were mixed 90 mL of $HNO_3$ (71%) and 12.6 g of gallium metal. The solution was blanketed with nitrogen and then heated to 65° C. After the metal had completely dissolved (3 days), the solution was cooled to 0° C. to form crystals of $Ga(NO_3)_3$. The crystals were recovered by filtration.

The recovered crystals were dissolved in 40 g of deionized water to which there was added an equal weight of ammonium hydroxide. A gelatinous white precipitate formed immediately. The solid was recovered by centrifugation and then washed twice with a 0.1 wt % solution of ammonium hydroxide.

EXAMPLE 3

Preparation of F—Ga-Smectite

A solution consisting of 3.86 g of NaF in 400 g of deionized water was mixed with a solution of 4.32 g of HF in 45 g of deionized water. To this solution there were added 30.36 g of fumed silica (manufactured by Cabot Co. and identified as Cabosil™) and 12.5 g of $Ga(OH)_3$ prepared as per Example 1. The resultant gel was stirred for 4 hours and then reacted in a Parr reactor at 200° C. for 2 days. The solid product was recovered by filtration, washed with one liter of deionized water and then dried at 110° C. X-ray diffraction of the dried powder showed it to be a smectite clay.

EXAMPLE 4

Preparation of F—Ga, Al-Smectite

A solution consisting of 3.86 g of NaF in 400 g of deionized water was mixed with a solution of 4.32 g of HF in 45 g of deionized water. To this solution there were added sequentially with heavy stirring, 30.36 g of fumed silica (manufactured by Cabot Co. and identified as Cabosil™), 17.4 g of AlOOH and 4.2 g of Ga(OH)$_3$ prepared as per Example 1. The resultant gel was stirred for 4 hours and then reacted in a Parr reactor at 200° C. for 5 days. The solid product was recovered by filtration, washed with one liter of water and dried at 100° C. X-ray diffraction of the product showed it to be a smectite clay.

EXAMPLE 5

A solution consisting of 3.86 g of NaF in 400 g of deionized water was mixed with a solution of 4.32 g of HF in 45 g of deionized water. To this solution there were added 30.36 g of fumed silica (manufactured by Cabot Co. and identified as Cabosil™) and 12.5 g of Ga(OH)$_3$ prepared as per Example 1. The resultant gel was stirred for 4 hours and then reacted in a Parr reactor at 150° C. for 2 days. The solid product was recovered by filtration, washed with one liter of deionized water and then dried at 110° C. X-ray diffraction of the dried powder showed it to be a smectite clay.

EXAMPLE 6

Preparation of F—Al, Fe-Smectite

A solution consisting of 3.86 g of NaF in 400 g of deionized water was mixed with a solution of 4.32 g HF in 45 g deionized water. To this solution there were added sequentially with mixing 30.36 g of fumed silica (Cabosil™), 17.4 g of AlOOH and 2.9 g of FeCl$_3$. The resultant gel was stirred for 4 hours and then reacted in a Parr reactor at 200° C. for 5 days. The solid product was recovered by filtration, washed with one liter of water and dried at 110° C. X-ray diffraction of the product showed the product to be a smectite clay.

EXAMPLE 7

Preparation of F—Ga, Al-Smectite

A solution consisting of 4.2 g of NaF in 400 g of deionized water was mixed with a solution of 3.98 g of HF in 45 g of deionized water. To this solution there were added sequentially with heavy stirring, 31.2 g of fumed silica (manufactured by Cabot Co. and identified as Cabosil™), 17.4 g of AlOOH and 14.9 g of Ga(OH)$_3$ prepared as per Example 2. The resultant gel was stirred for 4 hours and then reacted in a Parr reactor at 200° C. for 5 days. The solid product was recovered by filtration, washed with one liter of water and dried at 100° C. X-ray diffraction of the product showed it to be a smectite clay.

I claim as my invention:

1. A hydrocarbon conversion process comprising contacting a hydrocarbon feed under hydrocarbon conversion conditions with a catalyst to give a hydroconverted product, the catalyst comprising a smectite layered clay composition having the empirical formula $$A_x(M_yM'_{4-y})(Si_{8-t}M_tM'_v)O_{20}(OH)_{4-u}F_u$$

where A is a cation, x is the moles of the cation and varies from about 0.1 to about 2.0, M and M' are metals having a +3 oxidation state, each metal selected from the group consisting of aluminum, gallium, iron and chromium, y is the moles of M and varies from 0 to about 4, except that when M or M' is aluminum, y has a value from greater than 0 to about 4, t is the moles of M and varies from about 0 to about 2, v is the moles of M' and varies from about 0 to about 2 and t+v=x, and u is the moles of F and varies from about 0.1 to about 3.5.

2. The process of claim 1 further characterized in that the clay layers of the smectite clay are separated by pillars selected from the group consisting of alumina, rare earth containing alumina, $ZrO_2$, $TiO_2$, $Cr_2O_3$, $SiO_2$ and silica/alumina.

3. The process of claim 2 where the pillar is alumina.

4. The process of claim 2 where the pillar is a rare earth containing alumina.

5. The process of claim 1 where M is gallium and y is zero.

6. The process of claim 1 where M is iron and y is zero.

7. The process of claim 1 where M is chromium and y is zero.

8. The process of claim 1, where A is selected from the group consisting of alkali metals, quaternary ammonium ions, quaternary phosphonium ions and mixtures thereof.

9. The process of claim 8 where the quaternary ammonium ions are selected from the group consisting of tetramethylammonium ion, tetraethylammonium ion, tetrapropylammonium ion, tetrabutylammonium ion, tetra-t-butylammonium ion, tetrapentylammonium ion, tetraphenylammonium ion and mixtures thereof.

10. The process of claim 1 where the hydrocarbon conversion process is alkylation.

11. The process of claim 1 where the hydrocarbon conversion process is hydrocracking.

12. The process of claim 1 where the hydrocarbon conversion process is oligomerization.

* * * * *